United States Patent
Lindstrom

(10) Patent No.: US 8,425,481 B2
(45) Date of Patent: Apr. 23, 2013

(54) ATTACHMENT MEANS FOR AN INCONTINENCE PROTECTOR

(75) Inventor: Asa Lindstrom, Gothenburg (SE)

(73) Assignee: SCA Hygiene Products AB, Göteborg (SE)

( * ) Notice: Subject to any disclaimer, the term of this patent is extended or adjusted under 35 U.S.C. 154(b) by 369 days.

(21) Appl. No.: 12/740,621

(22) PCT Filed: Nov. 6, 2007

(86) PCT No.: PCT/SE2007/050820
§ 371 (c)(1),
(2), (4) Date: Apr. 29, 2010

(87) PCT Pub. No.: WO2009/061241
PCT Pub. Date: May 14, 2009

(65) Prior Publication Data
US 2010/0262111 A1    Oct. 14, 2010

(51) Int. Cl.
*A61F 13/15*    (2006.01)
(52) U.S. Cl.
USPC .............. 604/385.03; 604/385.24; 604/386; 604/387
(58) Field of Classification Search .......... 604/385.03, 604/385.01, 387
See application file for complete search history.

(56) References Cited

U.S. PATENT DOCUMENTS

| | | | |
|---|---|---|---|
| 5,037,417 A * | 8/1991 | Ternstrom et al. | 604/385.25 |
| 5,486,168 A | 1/1996 | Runeman et al. | |
| 5,843,065 A * | 12/1998 | Wyant | 604/385.09 |
| 6,129,719 A | 10/2000 | Nozaki et al. | |
| 6,409,712 B1 * | 6/2002 | Dutari | 604/385.09 |
| 6,565,548 B1 * | 5/2003 | Glaug et al. | 604/385.03 |
| 7,291,136 B1 * | 11/2007 | Drevik et al. | 604/385.03 |
| 7,553,300 B2 * | 6/2009 | Elfstrom et al. | 604/353 |
| 7,662,138 B2 * | 2/2010 | Hermansson et al. | 604/396 |
| 7,797,810 B2 * | 9/2010 | Hermansson | 29/469 |
| 8,052,663 B2 * | 11/2011 | Harsjo | 604/349 |
| 8,142,409 B2 * | 3/2012 | Reddy | 604/385.09 |

(Continued)

FOREIGN PATENT DOCUMENTS

CN 1197632 11/1998
DE 298 21 849 U1 3/1999

(Continued)

OTHER PUBLICATIONS

International Search Report (PCT/ISA/210) dated Jul. 24, 2008.

(Continued)

*Primary Examiner* — Susan Su
(74) *Attorney, Agent, or Firm* — Buchanan Ingersoll & Rooney PC

(57) ABSTRACT

A protector for male incontinent persons includes an absorbent body (1) enclosed between an inner liquid-permeable casing sheet (3) and an outer liquid-impermeable casing sheet (2) and having a crotch end part (7) and a front end part (6) opposite to the crotch end part. The front end part is wider than the crotch end part. The lateral sides of the protector are tapering from the front part to the crotch part so that the protector has a triangular shape. The protector also includes means (8,9) affixed to the outer liquid-impermeable casing sheet for attachment to an underwear. The attachment means at least includes a string of attachment means (8,9) extending along each tapering lateral side.

17 Claims, 1 Drawing Sheet

U.S. PATENT DOCUMENTS

| | | | |
|---|---|---|---|
| 2001/0031956 A1* | 10/2001 | Drevik | 604/385.04 |
| 2004/0111073 A1* | 6/2004 | Hermansson et al. | 604/349 |
| 2007/0060901 A1 | 3/2007 | Alletsee | |
| 2007/0255244 A1* | 11/2007 | Olsson et al. | 604/385.14 |
| 2008/0082072 A1 | 4/2008 | Helmfridsson et al. | |
| 2009/0182297 A1* | 7/2009 | Hedstrom et al. | 604/385.13 |
| 2010/0160885 A1* | 6/2010 | Cohen | 604/374 |
| 2010/0228217 A1* | 9/2010 | Harsjo | 604/385.03 |

FOREIGN PATENT DOCUMENTS

| | | | |
|---|---|---|---|
| GB | 2319730 A * | 6/1998 | |
| JP | 59-030217 U | 2/1984 | |
| JP | 2005-334348 A | 12/2005 | |
| JP | 2008-540028 A | 11/2008 | |
| WO | WO 2004/004617 A1 | 1/2004 | |
| WO | WO 2006/062444 A1 | 6/2006 | |
| WO | 2006/123973 A1 | 11/2006 | |
| WO | WO 2007/061341 A1 | 5/2007 | |

OTHER PUBLICATIONS

Written Opinion of the International Searching Authority (PCT/ISA/237) dated Jul. 24, 2008.

Official Action issued in corresponding Chinese Patent Application No. 200780101433.4, dated Jun. 5, 2012.

An English-language Translation of the Office Action (Notice of Reasons for Refusal) dated May 29, 2012, issued in corresponding Japanese Patent Application No. 2010-531986. (3 pages).

* cited by examiner

ATTACHMENT MEANS FOR AN INCONTINENCE PROTECTOR

TECHNICAL FIELD

The present invention relates to a protector for male incontinent persons including an absorbent body enclosed between an inner liquid-permeable casing sheet and an outer liquid-impermeable casing sheet and having a crotch end part and a front end part opposite to the crotch end part, said front end part being wider than said crotch end part, the lateral sides of the protector are tapering from the front part to the crotch part so that the protector has a triangular shape, the protector also including means affixed to the outer liquid-impermeable casing sheet for attachment to an underwear.

BACKGROUND OF THE INVENTION

A protector of the above mentioned type is known from WO 2007/061341 A1 and DE 298 21 849 U1. WO 2007/061341 A1 is concerned with the same problem as the present invention, namely to ensure a secure attachment of the protector to an underwear of a wearer while at the same time provide the attachment means at a reasonable cost. In WO 2007/061341 A1, a secure attachment is obtained by two strings of adhesive provided on the outer casing sheet, one transversely extended string of adhesive in a front part of the protector and a longitudinally extended string of adhesive in the rear part of the protector. The attachment of such a protector to underwear is normally safe and secure. However, under certain circumstances there is a risk that a protector will loose a portion or even the whole of its attachment to an underwear during use due to unsuitable movements of a the wearer, such as sitting with crossed-legs, or a not entirely correct application of the protector on the body of the wearer.

The objective of the present invention is to provide a protector of the type mentioned in the introductory paragraph having improved attachments means eliminating or at least greatly reducing problems related to movements of a user and also facilitating an application of such a protector to a user.

SUMMARY OF THE INVENTION

This objective is accomplished by a protector for male incontinent persons including an absorbent body enclosed between an inner liquid-permeable casing sheet and an outer liquid-impermeable casing sheet and having a crotch end part and a front end part opposite to the crotch end part, said front end part being wider than said crotch end part, the lateral sides of the protector are tapering from the front part to the crotch part so that the protector has a triangular shape, the protector also including means for attachment to an underwear affixed to the outer liquid-impermeable casing sheet, characterised in that said attachment means at least includes a string of attachment means extending along each tapering lateral side. By locating the attachment means along the inclined lateral sides of the protector, the risk for application of the protector to a wearer with the whole or portions of a side region in a folded in state is eliminated or at least greatly reduced. Moreover, the risk for folding in of the edges of side regions of the protector due to movements of a wearer is also essentially eliminated. A correct application of such a protector is also facilitated since the user must fold up possible folds or the like in the side portions of the protector in order to make an attachment of the attachment means to an underwear possible.

In the term "triangular shape" used above, a shape of a truncated triangle is included as well as triangular shapes with rounded edges and slightly curved sides.

According to a preferred embodiment said strings of attachment means are extended into the crotch part ending less than 50 mm, preferably less than 30 mm, and most preferably less than 20 mm from the end edge thereof. Thereby it is ensured that the strings are extended into the region in which the protector is influenced by movements of the wearer to the greatest extent. Preferably, the crotch ends of said strings of attachment means meet each other in the crotch part and thereby attain V-shape. Said strings of attachment means should preferably extend along 60-90%, preferably 70-90%, and more preferably 85-90% of the lateral sides of the protector.

In a second preferred embodiment, a further attachment means is located in the front end part and disposed between the end portions of the strings that extend along the lateral sides of the protector.

Said attachment means can be strings of adhesive, being continuous or discontinuous, which before use are protected by pieces of releaseable material.

Said attachment means can in a variant be strips of hooks material.

BRIEF DESCRIPTION OF THE DRAWING

The invention shall now be described with reference to the figures, of which.

DESCRIPTION OF EMBODIMENTS

Figure 1:
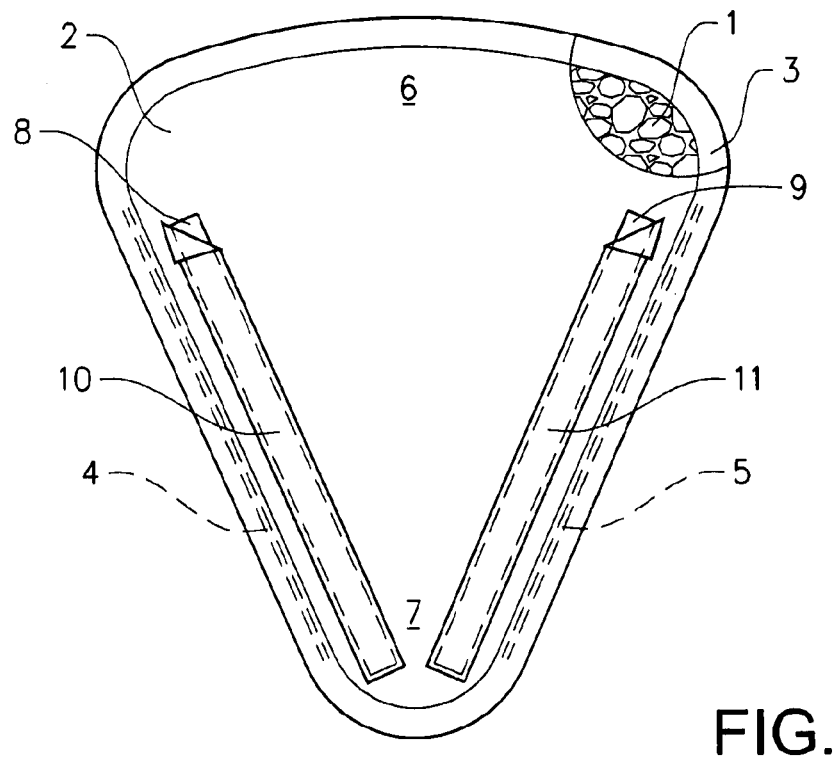
FIG. 1 shows a schematic plan view of a protector for male incontinent persons according to a first preferred embodiment of the invention, the outside of the protector, i.e. the side distal from a wearer in use, turned against the viewer, and a portion of the outer casing sheet being removed.

In FIG. 1 is schematically shown a protector for male incontinent persons. This protector includes an absorbent core 1 which is enclosed between an inner liquid permeable casing sheet 3 and an outer liquid impermeable casing sheet 2. The casing sheets are extended outside of the absorbent body 1 around the whole perimeter thereof and are affixed to each other in the portions extending outside of the absorbent body by suitable means, such as glue or weld seams. Elastic elements 4,5, such as one or more elastic threads or one elastic band, extend outside of and along each lateral side of the absorbent body and are affixed to a casing sheet or both casing sheets in an outstretched condition. Preferably, the elastic elements 4,5 are located between the casing sheets 2,3 and affixed to both of them in a suitable way, for example by gluing or heat welding.

The inner casing sheet, the outer casing sheet, the absorbent body and the elastic elements can be the same components as is known from WO 2007/061341 A1 having the same applicant as the present application, said publication is referred to for further details.

As an example, the inner casing sheet can be a spun-bond nonwoven, the outer casing sheet a microporous plastic film and the absorbent core can be a mixture of cellulosic fibres, so called fluff, and superabsorbent particles.

However, all materials and material combinations (laminations) used as inner casing sheets (top sheets) and all materials and material combinations (laminations) used as outer casing sheets (backing sheets) for incontinence protectors, diapers or sanitary napkins can be used in a protector according to the present invention. Furthermore, all materials known and combinations thereof for use in absorbent bodies for incontinence protectors, diapers or sanitary napkins can be used in a protector according to the present invention.

The protector in FIG. 1 is shown in a planar condition, i.e. with the elastic elements in a stretched condition. When the elastic elements are allowed to relax, their relaxation will cause the absorbent body to deform to an arcuate shape.

The front end part 6 of the protector, i.e. the upper end part of the protector shown in FIG. 1, is wider than a crotch end part 7, i.e. the lower end part shown in FIG. 1, and the lateral sides of the protector are tapering from the front part to the crotch part so that the protector has a triangular shape. The longitudinal direction of the protector is an imaginary line between the midpoints of the front and crotch end parts and a transverse direction is a direction perpendicular to the longitudinal direction. The lateral sides of the protector are thus inclined relative to both the longitudinal and the transverse direction. In use, after application of the protector on a wearer, the crotch end part of the protector is located between the legs of the user and reaches behind the penis and scrotum of the user.

According to the present invention, a string of adhesive 8,9 is affixed to the outer casing sheet 2 along each lateral side portion of the absorbent body 1. These strings of adhesive 8,9 have essentially the same inclination to the longitudinal and transverse directions as the lateral sides of the protector and are thus converging towards each other in a direction from the front end part edge of the protector to the crotch end part edge thereof. By a "string" is meant an elongate element having a length being at least twice its width.

By such a location of the strings of adhesive 8,9 the risk for lateral side portions of the absorbent body to be folded in towards the opposite lateral side is eliminated or at least greatly reduced. Such a folding in of said portions can occur due to certain movements of the wearer during use, such as crossing the legs while sitting. If the lateral side portions of the of the protector is free to move in relation to the underwear, there is a risk that such in-folds will still remain after the wearer has shifted position of the legs. In protectors, which are not attached to the underwear in the lateral side portions, there is also a risk that in-folds are created during the application of the protector if the user is not careful. With a protector according to the present invention such possible folds must be folded out in order to attach the protector to the underwear. By the present invention, a correct application of the protector in this respect is thereby facilitated and ensured.

If the outer casing sheet is permeable to air and vapour, which is preferred, the location of the strings of adhesive according to the present invention have an additional advantage, namely that the adhesive will not impair the permeability to air and vapour in the middle part of the protector where the need for this property is greatest.

Another advantage by the location of the adhesive strings according to the present invention is that the ability to stretch of the outer casing sheet and the underwear, to which the protector is attached, will not be influenced by a stiffening layer of adhesive in the middle part of the protector. Such stretching of the casing sheet and the underwear can take place due to swelling of the material in the absorbent body, especially if it contains a high percentage of so called superabsorbents (highly absorbent polymers). Since most of liquid will be emitted in the middle part of the absorbent body, the swelling would be largest there.

Since the forces due to movements of the wearer will be greatest in the crotch end part of the protector it is important that the strings of adhesive 8,9 are extended into this part. Preferably, the distance between the lower ends of the strings of adhesive 8,9 and the edge of the crotch end part, as viewed in FIG. 1, should not exceed 50 mm, preferably not 30 mm and most preferably not 20 mm.

In order to ensure that in-folds will not occur during use of the protector, the distance between the respective lateral edge of the absorbent body and the adjacent lateral edge of the associated string of adhesive 8,9 should preferably be less than 30 mm, and most preferably less than 20 mm.

In order to further eliminate the risk for in-folds and to ensure a secure attachment of the protector to the underwear of a wearer, the strings of adhesive 8,9 preferably also extend into the front end part of the protector. The strings of adhesive 8,9 extend along 60-90%, preferably 70-90%, and more preferably 85-90% of the length of the lateral sides of the protector.

The adhesive in strings 8,9 should preferably be a PSA (Pressure Sensitive Adhesive), for example an acrylate based adhesive or a hot melt adhesive. However, all types of adhesive used for attaching incontinence protectors or sanitary napkins to underwear can be used in the present invention. The surface weight of the adhesive will vary depending of the type of adhesive used but should preferably be between 15-40 $g/m^2$. If the surface weight is too high, the protector will adhere to strongly to the underwear and will be hard to loosen therefrom.

Each string of adhesive 8,9 are before used protected against dust and dirt by a release layer 10,11, for example a silicone coated paper strip or a strip of polyethylene film.

Figure 2:
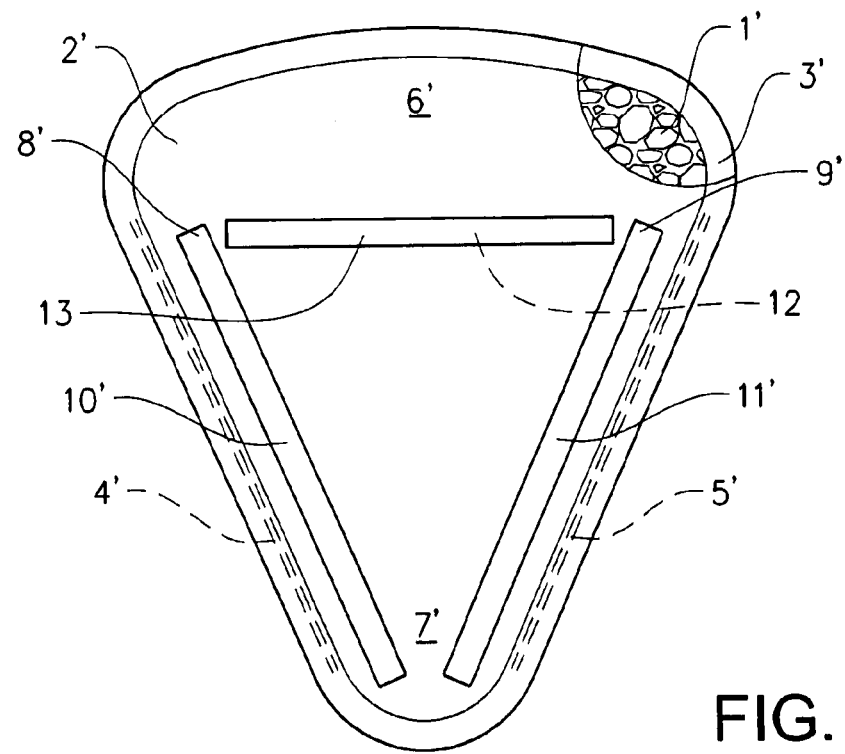
FIG. 2 shows a similar view as FIG. 1 of a protector according to a second preferred embodiment.

In FIG. 2 a second embodiment of a protector is shown in a view similar to the view in FIG. 1. The protector according to the second embodiment is in a lot of aspects similar to the protector according to the first embodiment and in the protector shown in FIG. 2 components similar to corresponding components in the protector according to the first embodiment shown in FIG. 1 are given the same reference numerals with the addition of a prime sign.

The protector according to the second embodiment differs from the protector according to the first embodiment in that a third string of adhesive 12 covered by a release layer 13 is affixed to the outer casing sheet 2'. This third string of adhesive has a transverse extension and is disposed in the front part of the protector. In the shown embodiment the string of adhesive 12 runs between the front ends of the strings 8',9' and the pattern of strings thereby attain the shape of a triangle. In the second embodiment the crotch ends of the lateral strings 8',9' meet each other so that these two strings together have a shape corresponding to the letter V. Thereby, the three strings of adhesive 8',9',12 together form a triangle. In all other respects, the protectors according to the first and second embodiment are the same.

By the additional transverse string of adhesive 12 the protector of the second embodiment is extremely securely attached to the underwear of a user. Since the transverse string of adhesive 12 is disposed in the front part of the protector, the middle region of the protector in which urine is most likely to be emitted, will not be adversely influenced by the strings of adhesive and the adhesive layers will not reduce air and vapour permeability in this area.

The string of adhesive 12 does not need to be located between the front ends of the lateral adhesive strings 8',9' but can of course be located nearer to the edge of the front end part 6' than in the shown example and even nearer the crotch part 7' of the protector, even if this is not preferred. The adhesive laterally disposed between the lateral adhesive strings need not be a string but can have a very limited transverse and longitudinal extension and be of any shape, such as rectangular, square, round, etc.

The embodiments shown can of course be modified without leaving the scope of invention. For example, can the lateral strings of adhesive in the first embodiment be located so that their ends in the crotch end part of the protector meet each other. Other attachment means than strings of adhesives for attaching the protector to underwear can be used, such as strips of hooks material such that the hooks have the capability to attach to the loops in the material of ordinary underwear. All or some of the adhesive strings can be continuous or discontinuous, for example can the lateral strings in the second embodiment be continuous while the transverse string be discontinuous in order to influence the stretchability and air and vapour permeability to a lesser extent. The discontinuity can consist of the strings forming "interrupted lines" or a pattern of spots of adhesive forming the strings. The invention shall therefore only be limited by the content of the enclosed patent claims.

The invention claimed is:

1. A protector for male incontinent persons, the protector comprising:
    an absorbent body enclosed between an inner liquid-permeable casing sheet and an outer liquid-impermeable casing sheet and having a crotch end part and a front end part opposite to the crotch end part, said front end part being wider than said crotch end part,
    lateral sides of the protector tapering from the front end part to the crotch end part so that the protector has a triangular shape, each of the lateral sides includes an elastic element extending substantially along the respective lateral side so as to provide the protector with a basin shape,
    an element affixed to the outer liquid-impermeable casing sheet for attachment to an underwear,
    wherein said element at least includes an elongated attachment element extending along each tapering lateral side, each attachment element extends along 60-90% of the lateral sides of the protector.

2. The protector according to claim 1, wherein said elongated attachment elements are extended into the crotch end part ending less than 50 mm from the end edge thereof.

3. The protector according to claim 2, wherein a distance between the respective lateral edge of the absorbent body and the adjacent lateral edge of the elongated attachment element is less than 30 mm.

4. The protector according to claim 2, wherein the crotch ends of said elongated attachment elements meet each other in the crotch end part and thereby attain a V-shape.

5. The protector according to claim 1, wherein said elongated attachment elements extend along 70-90% of the lateral sides of the protector.

6. The protector according to claim 1, wherein a further attachment element is located in the front end part and disposed between the end portions of the elongated attachment elements that extend along the lateral sides of the protector.

7. The protector according to claim 1, wherein said elongated attachment elements are strings of adhesive.

8. The protector according to claim 7, wherein said strings of adhesive are continuous.

9. The protector according to claim 7, wherein said strings of adhesive are discontinuous.

10. The protector according to claim 7, wherein the said strings of adhesive before use are protected by pieces of releaseable material.

11. The protector according to claim 1, wherein said elongated attachment elements are strips of hooks material.

12. The protector according to claim 2, wherein said elongated attachment elements are extended into the crotch end part ending less than 30 mm from the end edge thereof.

13. The protector according to claim 2, wherein said elongated attachment elements are extended into the crotch end part ending less than 20 mm from the end edge thereof.

14. The protector according to claim 3, wherein the distance between the respective lateral edge of the absorbent body and the adjacent lateral edge of the elongated attachment element is less than 20 mm.

15. The protector according to claim 3, wherein the crotch ends of said elongated attachment elements meet each other in the crotch end part and thereby attain V-shape.

16. The protector according to claim 5, wherein said elongated attachment elements extend along 85-90% of the lateral sides of the protector.

17. The protector according to claim 1, wherein the absorbent body comprises a mixture of cellulosic fibers and superabsorbent particles.

* * * * *